United States Patent
Miyawaki et al.

(10) Patent No.: US 8,198,072 B2
(45) Date of Patent: Jun. 12, 2012

(54) VIBRATION TYPE MICROINJECTION DEVICE

(76) Inventors: Fujio Miyawaki, Fujimi (JP); Kenji Kobayashi, Yokohama (JP); Jun Hasegawa, Hino (JP)

( * ) Notice: Subject to any disclaimer, the term of this patent is extended or adjusted under 35 U.S.C. 154(b) by 875 days.

(21) Appl. No.: 11/920,550

(22) PCT Filed: Jun. 16, 2006

(86) PCT No.: PCT/JP2006/312137
§ 371 (c)(1),
(2), (4) Date: Nov. 16, 2007

(87) PCT Pub. No.: WO2007/004407
PCT Pub. Date: Jan. 11, 2007

(65) Prior Publication Data
US 2009/0130743 A1    May 21, 2009

(30) Foreign Application Priority Data
Jun. 30, 2005   (JP) .................................. 2005-191613

(51) Int. Cl.
*C12M 1/26*   (2006.01)
*G01N 1/14*   (2006.01)
*H01L 41/09*   (2006.01)

(52) U.S. Cl. ..................... 435/285.1; 310/317; 310/328; 310/36; 73/863.01

(58) Field of Classification Search ............... 435/285.1; 310/36, 317, 328; 73/863.01
See application file for complete search history.

(56) References Cited

U.S. PATENT DOCUMENTS

| | | | | |
|---|---|---|---|---|
| 5,229,679 | A | 7/1993 | Higuchi | 310/328 |
| 6,193,010 | B1* | 2/2001 | Minto | 181/102 |
| 6,791,006 | B2* | 9/2004 | Nezu et al. | 800/18 |
| 2002/0116732 | A1* | 8/2002 | Christmann | 800/19 |

FOREIGN PATENT DOCUMENTS

| | | |
|---|---|---|
| JP | 63-299785 | 12/1988 |
| JP | 03-119989 | 5/1991 |
| JP | 06-090770 | 4/1994 |
| JP | 8-322568 | 12/1996 |
| JP | 2000-023657 | 1/2000 |
| JP | 2003-093898 | 4/2003 |
| JP | 2003-125750 | 5/2003 |
| WO | WO 01/19953 | 3/2001 |

OTHER PUBLICATIONS

F. Miyawaki et al, "Development of a Vibratory Microinjection Method", *The International Journal of Artificial Organs*, vol. 26, No. 1 (2003), pp. 80-85.

* cited by examiner

*Primary Examiner* — Nathan Bowers
*Assistant Examiner* — Gautam Prakash
(74) *Attorney, Agent, or Firm* — Bacon & Thomas, PLLC

(57) ABSTRACT

A vibration type microinjection device capable of ensuring smooth piercing of membranes having different properties such as a zona pellucida, a cell membrane and a nuclear membrane included in a fertilized egg with high accuracy and efficiency is provided.

A vibration type microinjection device comprises a vibrator (28) which is connected in series with a micropipette (8) and which has a piezoelectric actuator (29) installed in a housing, and a signal control device (21) for controlling an electric signal applied to the piezoelectric actuator (29), wherein vibration is applied in the longitudinal direction of the micropipette (8) via the vibrator (28) by inputting an electric signal to the piezoelectric actuator (29). By such configuration, smooth piercing of membranes having different properties such as a zona pellucida, a cell membrane and nuclear membrane included in a fertilized egg is realized with high accuracy and efficiency.

13 Claims, 11 Drawing Sheets

ELECTRIC INPUT

VIBRATION TYPE MICROINJECTION DEVICE

TECHNICAL FIELD

The present invention relates to a vibration type microinjection device.

BACKGROUND ART

Conventionally in this field, a micro movement device using a piezoelectric element (See Patent Document 1 below.), a micro manipulator using a driving force generator due to the piezoelectric element (See Patent Document 2 below.), and a microinjection device using the driving force generator due to the piezoelectric element (See Patent Document 3 below.) have been proposed. Furthermore, a method of piercing a membrane has been proposed (See Patent Document 4 below.). The method comprises the steps of bringing a membrane denaturing material, which undergoes a membrane denaturation reaction induced by a stimulus, into contact with a part of a membrane to be pierced or close thereto; stimulating the membrane denaturing material so as to denature the membrane; and piercing the membrane by using a membrane breaking material. Moreover, a microinjection device using a micropipette having a bent tip in a container such as a petri dish has been proposed. (See Patent Document 5 below.) In addition, a micro instrument for a micro manipulator comprising a micro instrument body having a fine edge at the tip on a processing side and a vibration means to give a vibration in the direction perpendicular to the axis of the micro instrument body has been proposed (See Patent Document 6 below.).
[Patent document 1]Japanese Patent Publication No. 63-299785.
[Patent document 2]Japanese Patent Publication No. 02-269583.
[Patent document 3]Japanese Patent Publication No. 03-119989.
[Patent document 4]WO 01/019953.
[Patent document 5]Japanese Patent Publication No. 2003-125750.
[Patent document 6]Japanese Patent Publication No. 06-090770.

DISCLOSURE OF INVENTION

Said micro manipulator and microinjection device having a micro movement mechanism as disclosed in the above patent documents 1 to 3, however, have a driving mechanism of mainly straight motion due to driving by a piezoelectric element.

Said method of piercing a membrane as disclosed in the above patent document 4 uses a membrane denaturation reaction induced by stimulation application. However, for microinjection using a micropipette in a case where a foreign DNA is injected into a fertilized egg, such method giving rise to a membrane denaturation is not preferred.

Furthermore, in the conventional method as disclosed in the above patent document 5, a precise operation of the micropipette was difficult because of the bent tip of the micropipette.

Moreover, such micropipette having a bent tip has a difficulty in vibrating the tip in its longitudinal direction.

In addition, there is a problem in the method disclosed in the above patent document 6, where a manipulator is driven by its stage, that the driving frequency is limited to a low frequency range.

In view of the above problems, the present invention provides a vibration type microinjection device capable of making smooth piercing to membranes of different properties such as a zona pellucida, a cell membrane and a nuclear membrane included in a fertilized egg with high accuracy and efficiency.

The present invention also provides a vibration type microinjection device capable of making smooth piercing to a membrane even by using a micropipette having a bend at the tip by giving vibration in the longitudinal direction of the bent tip portion of the micropipette.

In order to achieve the objects described above, the present invention provides the following.

[1] A vibration type microinjection device comprising: a vibrator 1 which is connected in series with a micropipette 8 and which has a piezoelectric actuator 2 installed in a housing 3; and a signal control device for controlling an electric signal applied to the piezoelectric actuator 2, wherein vibration is applied in the longitudinal direction of the micropipette 8 via the vibrator 1 by inputting an electric signal to the piezoelectric actuator 2.

[2] In the vibration type microinjection device described in the above [1], the vibrator 1 comprises a path 4 formed in the center part of the vibrator 1; the housing 3 made of elastically deformable material; and the piezoelectric actuator 2 installed in the housing 3 to apply vibration to the housing 3.

[3] In the vibration type microinjection device described in the above [1], the shape of the piezoelectric actuator 2 is cylindrical.

[4] In the vibration type microinjection device described in the above [1], the signal control device 21 comprises at least a variable frequency oscillator 22; an amplifier for amplitude adjustment 23 connected to the variable frequency oscillator 22; a switch 24 connected to the amplifier for amplitude adjustment 23; and an adder 26 to which the switch 24 and a variable DC source for offset adjustment 25 are connected, and contains a power amplifier 27 which is connected to the adder 26 and which supplies an electric signal to the piezoelectric actuator 29.

[5] In the vibration type microinjection device described in the above [4], the signal control device comprises a plurality of the variable frequency oscillators 42, 44; and a switch 46 of a change-over type, whereby changeover to any one of the plurality of the variable frequency oscillators 42, 44 is carried out by switching the switch of a change-over type 46.

[6] In the vibration type microinjection device described in the above [1], the signal control device comprises at least a plurality of variable frequency oscillators A1, A2, . . . AN; a plurality of amplifiers for amplitude adjustment B1, B2 . . . BN connected to the plurality of variable frequency oscillators A1, A2 . . . AN; a first adder C1 to which output signals from the plurality of amplifiers for amplitude adjustment B1, B2 . . . BN are inputted simultaneously; a switch S connected to the first adder C1; and a second adder C2 connected to the switch S and a variable DC source for offset adjustment D, and contains a power amplifier E connected to the second adder C2 to supply an electric signal to the piezoelectric actuator, thereby simultaneously supplying vibration with a plurality of frequencies.

[7] In the vibration type microinjection device described in the above [1], the vibration type microinjection device comprises a multiple change-over type switch 51; a circuit for applying bias voltage 52 connected to the multiple change-over type switch 51; a computer 53 connected to the circuit for applying bias voltage 52; a DA converter 54 connected to the computer 53, and contains a power amplifier 55 which is connected to the DA converter 54 and which supplies an electric signal to the piezoelectric actuator.

[8] In the vibration type microinjection device described in the above [1], the vibration type microinjection device comprises a microscope 68 with an imaging device 69 to take an image of the tip of the micropipette 63; an image input interface 70 to input the image from the imaging device 69; a computer 65 to input a digital output signal from the image input interface 70; and a DA converter 66 connected to the computer 65, and contains a power amplifier 67 which is connected to the DA converter 66 and which supplies an electric signal to the piezoelectric actuator 62, wherein the electric signal from the power amplifier 67 is controlled according to the position of the tip part of the micropipette 63.

[9] In the vibration type microinjection device described in the above [8], the micropipette 63 starts vibrating from when the tip of the micropipette 63 comes into a predetermined distance from a processing object 71, and while keeping its vibration, the tip of the micropipette 63 is inserted into the processing object 71, and the vibration condition is controlled while the tip of the micropipette remains inside the processing object 71.

[10] In the vibration type microinjection device described in the above [9], the processing object 71 is a fertilized egg and the vibration condition is adjusted (controlled) depending on objects to be pierced: a zona pellucida or a nuclear membrane of the fertilized egg.

[11] In the vibration type microinjection device described in the above [9], the processing object 71 is a fertilized egg and the vibration condition is adjusted (controlled) depending on objects to be pierced: a cell membrane or a nuclear membrane of the fertilized egg.

[12] A vibration type microinjection device comprising a vibrator 100 which is connected in series with a micropipette 108 and which has a plurality of piezoelectric actuators 101, 102 installed in a housing 3; and a signal control device 120 for controlling electric signals applied to the piezoelectric actuators 101, 102, wherein vibration is applied at least in the longitudinal direction of the micropipette 108 via the vibrator 100 by inputting electric signals to the piezoelectric actuators 101, 102.

[13] In the vibration type microinjection device described in the above [12], the vibrator comprises a path 104 formed in the center part of the vibrator 100; the housing 103 made of elastic material; and a plurality of pillar type piezoelectric actuators 101, 102 installed in the housing 103 in the direction to the micropipette 108.

[14] In the vibration type microinjection device described in the above [13], the tip of the micropipette 108 is bent 108A, and the signal control device 120 comprises at least: a variable frequency oscillator 121; a first amplifier for amplitude adjustment 122 connected to the variable frequency oscillator 121; a first switch 123 connected to the first amplifier for amplitude adjustment 122; a first adder 125 connected to the first switch 123 and a first variable DC source for offset adjustment 124; a variable phase shifter 127 connected to the variable frequency oscillator 121; a second amplifier for amplitude adjustment 128 connected to the variable phase shifter 127; a second switch 129 which is connected to the second amplifier for amplitude adjustment 128 and which operates simultaneously with the first switch 123; a second adder 131 connected to the second switch 129 and a second variable DC source for offset adjustment 130, and contains a first power amplifier 126 connected to the first adder 125 and a first piezoelectric actuator 101, and a second power amplifier 132 connected to the second adder 131 and a second piezoelectric actuator 102, whereby vibration is applied to the bent part 108A of the tip of the micropipette 108 in the longitudinal direction of the bent part.

[15] In the vibration type microinjection device described in the above [13], the tip of the micropipette 108 is bent 108A, and the signal control device 220 comprises at least: a first amplifier for amplitude adjustment 222 connected to a first variable frequency oscillator 221; a first adder 223 which is connected to the first amplifier for amplitude adjustment 222 and to which an output signal from a second amplifier for amplitude adjustment 236 connected to a second variable frequency oscillator 235 is applied; a first switch 224 connected to the first adder 223; and a second adder 226 connected to the first switch 224 and a first variable DC source for offset adjustment 225, and further comprises the first variable frequency oscillator 221; a first variable phase shifter 228 connected to the first variable frequency oscillator 221; a third amplifier for amplitude adjustment 229 connected to the first variable phase shifter 228; a third adder 230 connected to the third amplifier for amplitude adjustment 229 and a fourth amplifier for amplitude adjustment 238 connected to a second variable phase shifter 237 to which the second variable frequency oscillator 235 is connected; a second switch 231 which is connected to the third adder 230 and which operates simultaneously with the first switch 224; and a fourth adder 233 connected to the second switch 231 and a second variable DC source for offset adjustment 232; and moreover comprises a first power amplifier 227 which is connected to the second adder 226 and which supplies an output signal to a first piezoelectric actuator 211; and a second power amplifier 234 which is connected to the fourth adder 233 and which supplies an output signal to a second piezoelectric actuator 212, whereby vibration is applied to the bent part 108A of the tip of the micropipette 108 in the directions parallel and perpendicular to the longitudinal direction of the bent part.

[16] In the vibration type microinjection device described in the above [14] or [15], an imaging device 311 is provided to take image of the bend 304 at the tip of the micropipette 303, image information from the imaging device 311 is taken into a computer 312, and the signal control device 313 is controlled with the computer 312 according to the information about position and angle of the bend 304 at the tip of the micropipette 303 detected by the image analysis to drive each of the plurality of piezoelectric actuators 301, 302, thereby enabling automatic setting of amplitudes, frequencies and phases of the vibrations given to the tip of the micropipette 303 corresponding to the position and angle of the bend 304 at the tip of the micropipette 303.

[17] In the vibration type microinjection device described in the above [16], the vibration type microinjection device comprises an imaging device 311 to take image of the bend 304 at the tip of the micropipette 303; and an imaging device 322 to detect a fertilized egg and the tip of the micropipette 303, wherein image information from the imaging devices 311, 322 are taken into a computer 312, the signal control device 313 is controlled with the computer 312 according to the information about position and angle of the bend 304 at the tip of the micropipette 303 detected by the image analysis and the detected information on the fertilized egg and the tip of the micropipette 303 to drive each of the plurality of piezoelectric actuators 301, 302, thereby enabling detection of positions of the fertilized egg and the tip of the micropipette 303 and automatic control of the vibrations given to the micropipette 303.

[18] In the vibration type microinjection device described in the above [14] to [17], a circular or elliptical vibration is applied to the micropipette.

[19] In the vibration type microinjection device described in the above [1] to [18], an amplitude of a vibration is sub-micron to micron order and a frequency is within the range from audible to ultrasonic range.

[20] In the vibration type microinjection device described in the above [1] to [18], at least one of vibrations has a frequency in the ultrasonic range.

BEST MODE FOR CARRYING OUT THE INVENTION

A vibration type microinjection device according to the present invention is composed of a vibrator which is connected to a micropipette and which contains a piezoelectric actuator; and a signal control device for controlling an electric signal applied to the piezoelectric actuator, whereby vibration is applied in the longitudinal direction of the micropipette by inputting an electric signal to the vibrator. Accordingly, the present invention enables;

(1) inserting the tip portion of the micropipette smoothly into the membrane of a processing object such as a fertilized egg by controlling vibration applied to the tip portion of the micropipette in its longitudinal direction.

(2) applying vibration so as to move the tip of the micropipette approximately parallel to and/or perpendicular to the axis of the tip and/or also so as to move the tip circularly and/or elliptically, even when the tip of a micropipette is bent.

Embodiments

Embodiments of the present invention are described in detail in the following.

Figure 1:
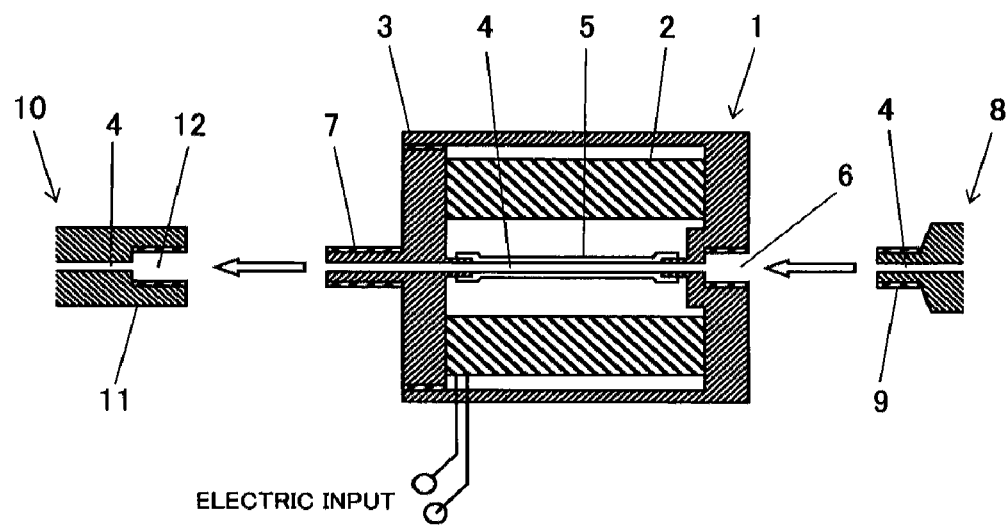
FIG. 1 is a schematic diagram of a structure of a vibrator of a vibration type microinjection device in accordance with a first embodiment of the present invention.
Figure 2:
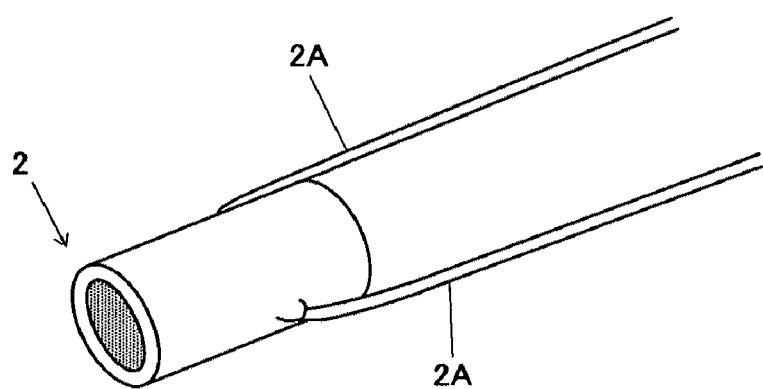
FIG. 2 is a perspective view of a cylindrical shape piezoelectric actuator of the vibration type microinjection device in accordance with the first embodiment of the present invention.

FIG. 1 is a schematic diagram of a structure of a vibrator of a vibration type microinjection device in accordance with the first embodiment of the present invention, and FIG. 2 is a perspective view of a piezoelectric actuator of the vibration type microinjection device.

In these figures, 1 is a vibrator comprising a piezoelectric actuator 2 (such as a cylindrical multilayer piezoelectric actuator as shown in FIG. 2) and a housing 3 made of elastically deformable material (such as duralumin) which houses the piezoelectric actuator. This housing 3 has a TEFLON™-tube 5 with a narrow path 4 formed at the center. At one end of the housing 3, a fitting concave 6 is formed to be fitted with the base part of the micropipette 8, and at the other end of the housing 3, a fitting convex 7 is formed to fit an injection controller part 10. Besides, on the base part of the micropipette 8, a fitting convex 9 to fit the fitting concave 6 described above and a small path 4 are formed. At an end part 11 of the injection controller part 10, fitting concave 12 to be fitted with the fitting convex 7 described above and a small path 4 are formed. When the injection controller part 10, the vibrator 1 and the micropipette 8 are all connected, the path 4 is brought into line on their center axis.

The piezoelectric actuator 2, the detail of which is described later, is configured so that an electric input is applied externally via lead wires 2A. The piezoelectric actuator 2 is, for example, a multilayer piezoelectric actuator, which utilizes a ceramic element (made by NEC Tokin co.) capable of converting electric energy to mechanical energy such as displacement or force by making use of the piezoelectric longitudinal effect. Since the multilayer piezoelectric actuator uses piezoelectric ceramic materials with high electrostrictive factors, it is compact and capable of generating larger displacement/force at lower voltage as compared with the conventional piezoelectric actuator.

In addition, the vibrator 1 has a structure as shown in FIG. 1, in which the piezoelectric actuator 2 is fitted into the housing 3 and the vibrator 1 is interposed between the main body of the conventional microinjection apparatus and the micropipette 8 when used. By such configuration, the periodical expansion and contraction of the piezoelectric actuator 2 is transmitted to the housing 3, thereby vibrating the micropipette 8 attached to the vibrator 1 parallel to the longitudinal axis of the micropipette 8. Through the use of the multilayer piezoelectric actuator as described above as a piezoelectric actuator 2, it becomes possible to apply vibration in the order from sub-micron to micro meter. In particular, by using a multilayer piezoelectric actuator with a cylindrical shape, well balanced vibration with symmetry in the longitudinal direction of the micropipette can be applied. This type of vibrator 1, unlike the resonance type vibrator commonly used in the ultrasonic equipments and devices, enables being driven in a wide frequency range and being driven at any combination of multiple frequencies.

Experimental results obtained by using the vibration type microinjection device wherein said type of vibrator according to the present invention is used are described in the following.

In the experiment, frequency in the vibration type microinjection method was set at 5 kHz and applied voltage was set at 15V. For comparison, reference was taken from experimental results obtained by using the conventional microinjection method (with no vibration type). Fluorescent protein Venus was used as a recombinant DNA, and BDF1 mice were used. In addition, the device is, at present, in a stage that the continuously variable frequency range is below 15 kHz, and the amplitude is also variable within some range, and is capable of being adjusted by applied voltage.

In the experiment, Venus gene solution was put into an injection pipette. After applying vibration for 1 hour with the vibration condition described above, the Venus solution was electrophoresed. Then, no fragmentation of the Venus genes was confirmed.

The randomized injection experiment was performed and evaluated after fertilized eggs obtained from the mice had evenly been divided into several sets. In each set, injection was performed by using one pipette, and a total of 14 sets of fertilized eggs were manipulated. The number of manipulated eggs was 470 in each group (vibration and non-vibration groups). Cases where no recombinant DNA was injected during injection and where something wrong with the vibrator happened were excluded from evaluation.

The following results were obtained from the experiment.

(a) Deformation rate of fertilized eggs at the time of being pierced: Deformation rate of fertilized eggs at the time of being pierced with a micropipette was 32.7±6.0% in the case where a non-vibration type microinjection was carried out, and 26.2±5.9% in the case where a vibration type microinjection was performed. Thus, the vibration type microinjection according to the present invention resulted in a lower deformation rate than the conventional non-vibration type injection did.

(b) Development rate of fertilized eggs: The state of development of manipulated eggs in cell culture medium was observed for 4 days after injection. (Cultured eggs do not develop over the stage of blastocyst, and it takes about 4 days to reach the blastocyst stage.) When non-vibration type microinjection was performed, 72 out of 465 eggs (15.5%) reached the blastocyst stage, and 30 out of them (6.5% out of all the manipulated eggs) expressed Venus proteins. On the other hand, when vibration type microinjection was performed, 87 out of 305 eggs (28.5%) reached the blastocyst stage, and 27 out of them (8.9% out of all the manipulated eggs) expressed Venus proteins. It is obvious that the microinjection performed by using the vibration type microinjection according to the present invention can make the eggs develop into the blastocyst stage more significantly.

Furthermore, the event of pulling out the nuclear DNA was observed in 6 pipettes out of 14 (43%) during non-vibration type microinjection, but it was in only 2 pipettes out of 14 (14%) during vibration type microinjection according to the present invention.

It is considered that the above results demonstrate effectiveness of the vibration type microinjection device according to the present invention.

The following is an explanation about the signal control device for driving the vibrator used in the vibration type microinjection device according to the present invention.

Figure 3:
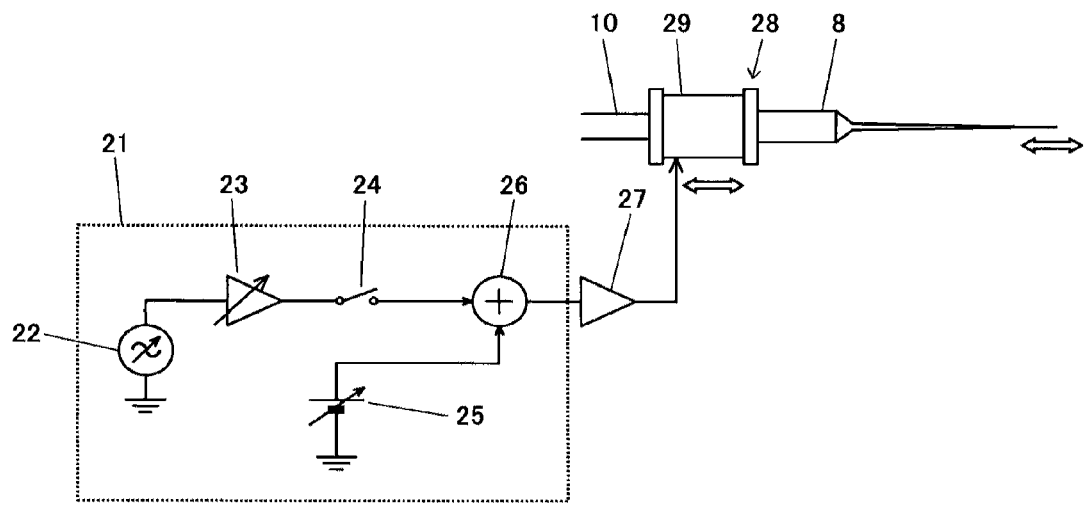
FIG. 3 is a configuration diagram of a first signal control device which forms a base of the present invention.

FIG. 3 is a configuration diagram of a first signal control device which forms a base of the present invention.

In this figure, the signal control device 21 comprises a variable frequency oscillator 22, an amplifier for amplitude adjustment 23 connected to the variable frequency oscillator 22, a foot switch 24 connected to the amplifier for amplitude adjustment 23, a DC source for offset adjustment 25, and an adder 26 to which the output from the foot switch 24 and the output from the DC source for offset adjustment 25 are inputted and which is connected to a DC coupling power amplifier 27, and an output signal from this power amplifier 27 is applied to a multilayer type piezoelectric actuator 29 in a vibrator 28.

In general, a multilayer type piezoelectric actuator 29 is strong against compressive force, but weak against expansive force. Therefore, as shown in FIG. 3, a DC voltage (for offset adjustment) generated in the DC source for offset adjustment 25 is applied in advance to the multilayer type piezoelectric actuator 29 so as to keep the multilayer type piezoelectric actuator 29 compressive before the multilayer type piezoelectric actuator 29 is vibrated.

In other words, the signal control device 21 comprises the variable frequency oscillator 22 to generate a signal for applying vibration, the amplifier for amplitude adjustment 23, the DC source for offset adjustment 25, and the adder 26, and thereby drives the vibrator 28 through the DC coupling power amplifier 27. Since the vibration is necessary only when the zona pellucida of a fertilized egg or nuclear membrane is pierced, vibration is applied by using a foot switch 24 or the like only when it is necessary. However, if the DC component is turned off as well as the AC component while the foot switch 24 is off, this results in displacement of the micropipette. In order to avoid this displacement, it is configured that the offset voltage is always applied to the vibrator 28 even when the foot switch 24 is off.

The following is an explanation about the structure of a fertilized egg which is an object for the microinjection.

Figure 4:
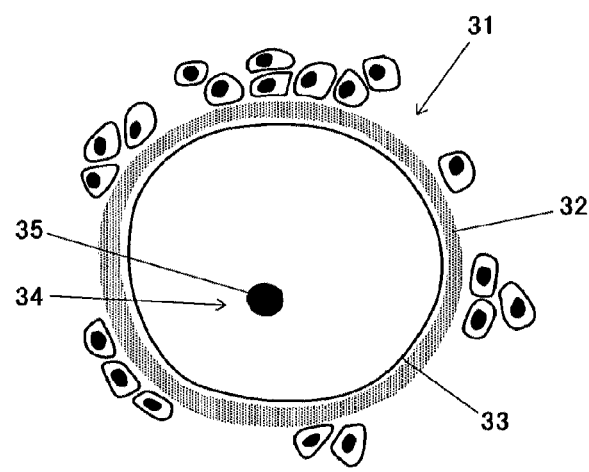
FIG. 4 is a schematic diagram showing a fertilized egg.
Figure 5:
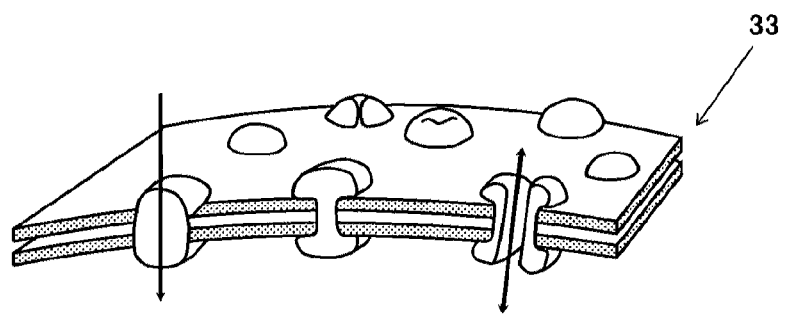
FIG. 5 is a schematic diagram showing a structure of cell membrane of a fertilized egg.
Figure 6:
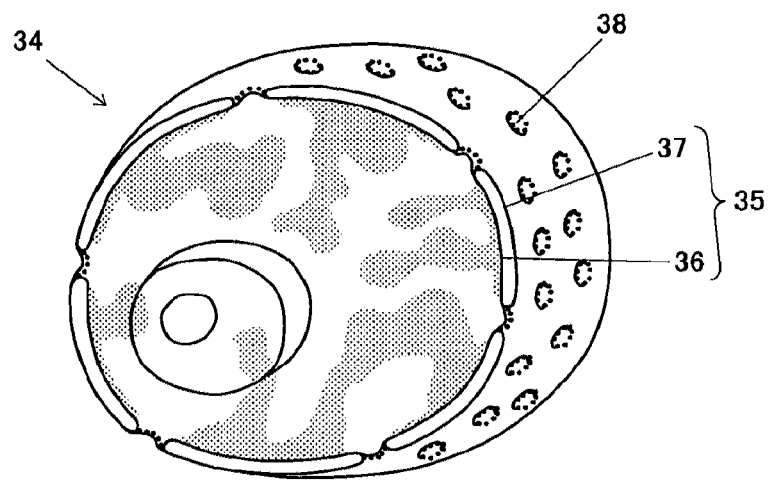
FIG. 6 shows a schematic diagram showing a nucleus and a nuclear membrane of a fertilized egg.
Figure 7:
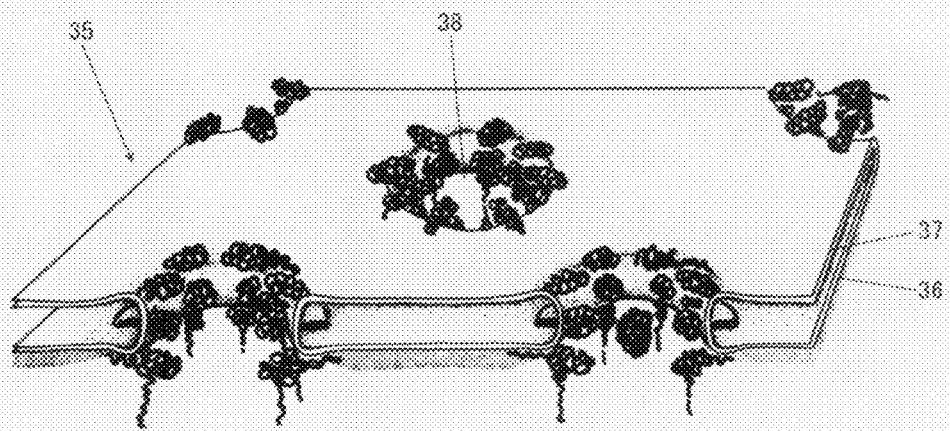
FIG. 7 shows a schematic diagram showing a nuclear membrane and holes in the nuclear membrane of a fertilized egg.
Figure 8:
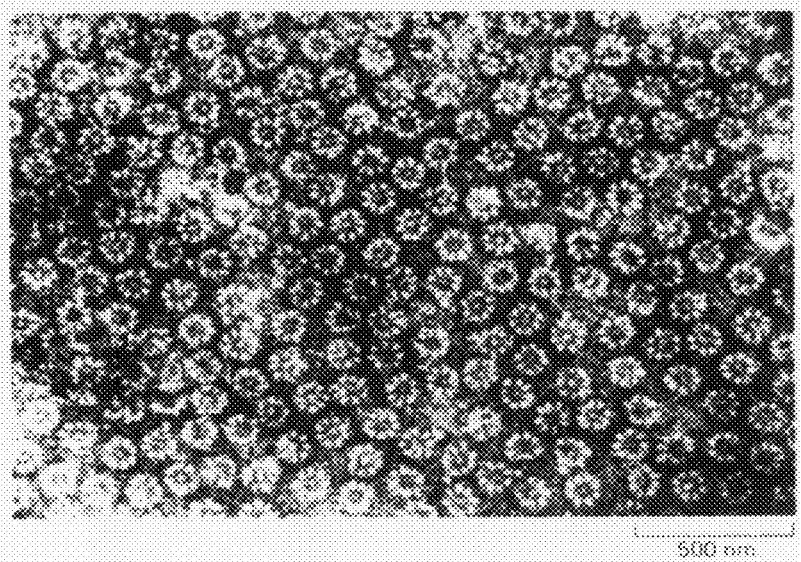
FIG. 8 is an electron micrograph of a nuclear membrane and holes in the nuclear membrane of a fertilized egg.

FIG. 4 is a schematic diagram showing a fertilized egg. FIG. 5 is a schematic diagram showing a structure of its cell membrane. FIG. 6 shows schematic diagram showing a nucleus and its nuclear membrane. FIG. 7 shows a schematic diagram showing a nuclear membrane and holes in the nuclear membrane. FIG. 8 is an electron micrograph of a nuclear membrane and holes in the nuclear membrane.

Three types of membranes (zona pellucida, cell membrane, nuclear membrane) must be pierced before the micropipette enters a nucleus 34 of a fertilized egg 31. Structures of these three types of membranes are completely different from each other.

The outermost layer of the fertilized egg 31 is covered with a layer called zona pellucida 32. This zona pellucida 32 of a murine ovum has a thickness of about 7 μm, is structureless, and has glycoprotein as a main component. A nucleus 34 can be seen approximately at the center of the fertilized egg 31.

Cell membrane 33 exists just inside the zona pellucida 32. The cell membrane 33 of the fertilized egg 31 is the same as the cell membrane of ordinary cells. As shown in FIG. 5, phospholipid molecules are arranged in double-layered structure (lipid bilayer) to constitute a single-layered cell membrane 33. There are a lot of proteins in the cell membrane 33.

The nucleus 34 is covered with a nuclear membrane 35 and is separated from the cytoplasm. As shown in FIG. 6 and FIG. 7, the nuclear membrane 35 consists of an inner membrane 36 and an outer membrane 37 each of which has the same basic structure as the cell membrane 33 and is constituted of a lipid bilayer. In the nuclear membrane 35, there are many pores called nuclear pore 38. Through the nuclear pore 38, proteins are movable between the nucleus 34 and cytoplasm. To summarize structural difference between the nuclear membrane 35 and the cell membrane 33, the nuclear membrane 35 is constituted of a double lipid bilayer, whereas the cell membrane 33 is constituted of a single lipid bilayer. Many nuclear pores 38 approximately 100 nm in diameter can be seen in FIG. 8.

In summary, the zona pellucida 32, i.e. the outermost layer of the fertilized egg 31, is a relatively hard membrane, whereas the cell membrane 33 is a lipid membrane with high fluidity. The nuclear membrane 35 is a double layer membrane, each single layer of which is almost the same as the cell membrane. As can be understood from the aforementioned explanation, the resistances of these three types of membranes are different from each other when they are pierced with a micropipette. Especially, it is said that the nuclear membrane 35 has the largest resistance among three of them.

As described above, since the resistances against penetration of the zona pellucida 32, the cell membrane 33 and the nuclear membrane 35 of the fertilized egg 31 are different from each other when they are pierced, the optimal frequencies and amplitudes of vibration for penetrating the respective membranes can be different. From this viewpoint, a second signal control device is configured in the following manner.

Figure 9:
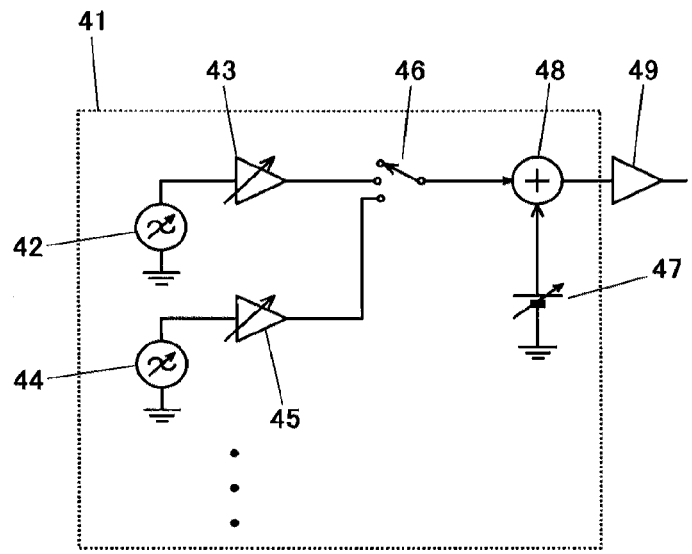
FIG. 9 is a configuration diagram of a second signal control device which forms a base of the present invention.

FIG. 9 is a configuration diagram of the second signal control device which forms a base of the present invention.

As shown in this figure, the signal control device 41 comprises a first variable frequency oscillator 42, a first amplifier for amplitude adjustment 43 connected to the first variable frequency oscillator 42, and moreover a second variable frequency oscillator 44, a second amplifier for amplitude adjustment 45 connected to the second variable frequency oscillator 44, a two-stage change-over type foot switch 46 which selectively connects to either the first amplifier for amplitude adjustment 43 or the second amplifier for amplitude adjustment 45, a DC source for offset adjustment 47, and an adder 48 to which the output from the foot switch 46 and the output from the DC source for offset adjustment 47 are inputted. The adder 48 is connected to a DC-coupling power amplifier 49 and the output signal from the power amplifier 49 is applied to a multilayer type piezoelectric actuator of a vibrator (not shown).

Figure 10:
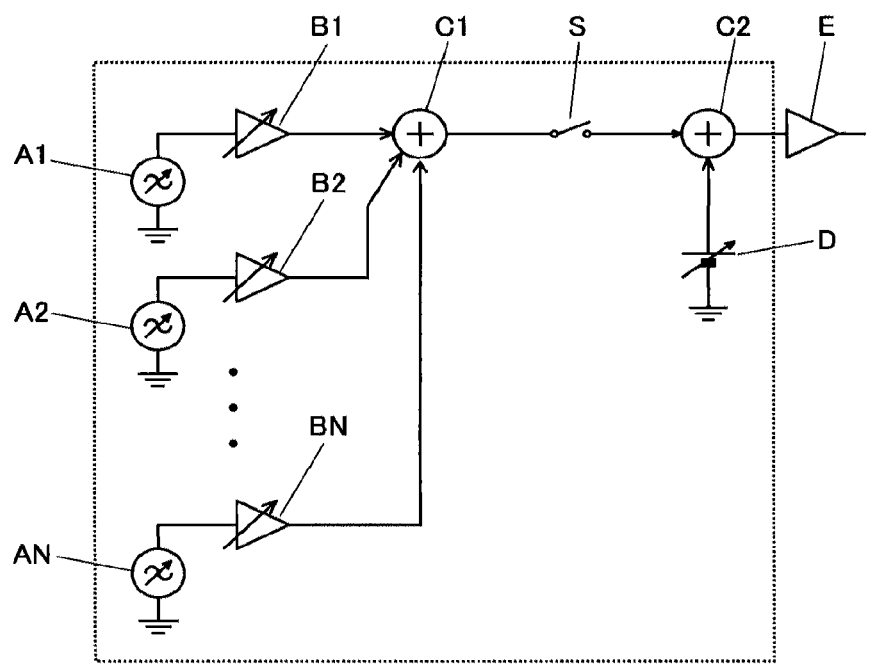
FIG. 10 shows a modified version of a signal control device which forms a base of the present invention.

Then, as shown in FIG. 9, by using the two-stage changeover type foot switch 46 and the like, instantaneous changeover between the first and the second sets of variable frequency oscillator and amplifier for amplitude adjustment is performed for optimization. Such changeover may be performed at the level of the entire circuit as shown in FIG. 9, or only at the level of element components (such as resistors, dip switches and the like) for controlling the frequency and the amplitude. Furthermore, the optimization can be realized by inputting vibration signals, which are generated and adjusted by a plurality of variable frequency oscillators A1-AN and amplifiers for amplitude adjustment B1-BN, simultaneously to the adders C1, C2 as shown in FIG. 10. Furthermore, the optimization by a combination of FIG. 9 and FIG. 10 can be also considered. Here, S stands for a switch, D for a DC source for offset adjustment, and E for a DC-coupling power amplifier.

Figure 11:
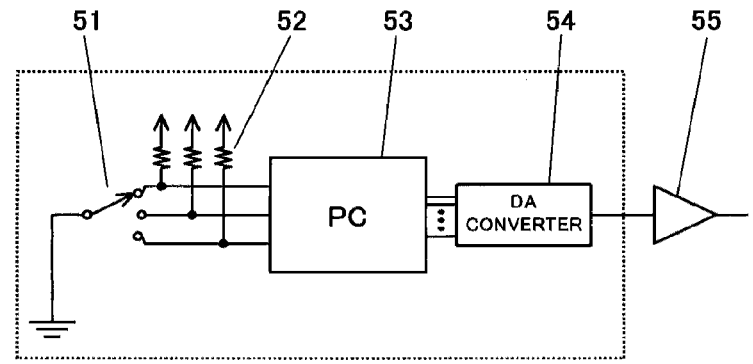
FIG. 11 is a configuration diagram of a third signal control device which forms a base of the present invention.

The signal control device of this embodiment can be also realized by a combination of a personal computer and a DA converter as shown in FIG. 11.

FIG. 11 is a configuration diagram of a third signal control device which forms a base of the present invention.

In this figure, 51 is a multi-stage change-over type foot switch, 52 is bias resistors, 53 is a personal computer, 54 is a DA converter, and 55 is a DC-coupling power amplifier.

As shown in this figure, signals generated according to connection made with the multi-stage change-over type foot switch and the like are applied to the personal computer 53, an output signal in response to the situation is calculated by the personal computer 53, and the output from the DA converter 54 drives the vibrator (not shown) through the power amplifier 55.

Timing for applying vibration or changing frequency and the like may be performed with the foot switch. Further improvement in operating efficiency can be realized by processing the image obtained from a microscope with a personal computer in order to extract contours of the fertilized egg and the tip of the pipette and thus in order to calculate their relative positions, and by controlling the vibration state automatically according to the calculated result.

Figure 12:
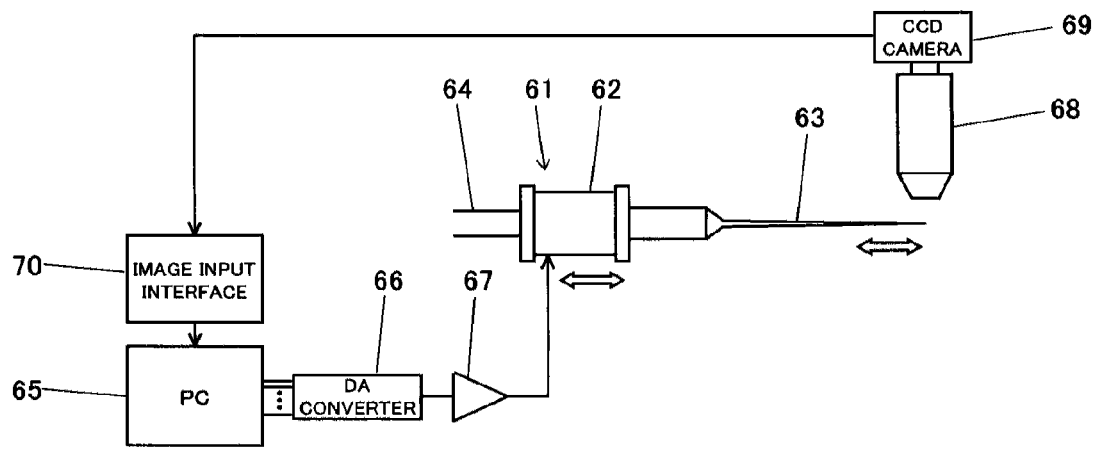
FIG. 12 is a schematic diagram of a control system of vibration using an image processing according to an embodiment of the present invention.
Figure 13:
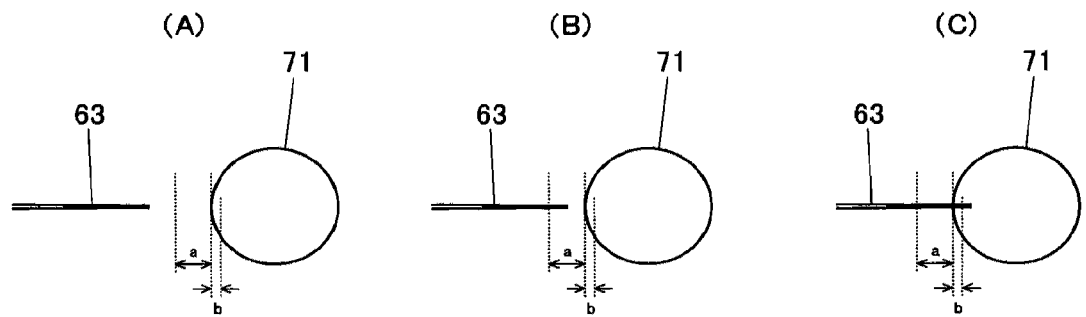
FIG. 13 shows an image of control performed by the control system of vibration using the image processing according to an embodiment of the present invention.

FIG. 12 is a schematic diagram of a control system of vibration using an image processing according to an embodiment of the present invention. FIG. 13 shows an image of the control.

In these figures, 61 is a vibrator, 62 is a piezoelectric actuator of the vibrator, 63 is a micropipette, 64 is an injection controller part, 65 is a personal computer, 66 is a DA converter, 67 is a DC-coupling power amplifier, 68 is a microscope with a CCD camera 69, 70 is an image input interface connected to the CCD camera 69. The image input interface 70 is connected to the personal computer 65. Furthermore, in FIG. 13, 71 is a fertilized egg.

An image of the tip of the micropipette 63 and fertilized egg 71 is taken by the CCD camera 69 connected to the microscope 68 and is sent to the personal computer 65 through the image input interface 70. In the personal computer 65, contours of the tip of the micropipette 63 and the fertilized egg 71 are extracted from the image. In this processing, the ordinary image processing technology such as differentiation method or the like is used.

As shown in FIG. 13(A), with no vibration applied to the micropipette 63, the micropipette 63 is brought close to the fertilized egg 71, and when the distance between the fertilized egg 71 and the tip of the micropipette 63 gets shorter than a predetermined value a as shown in FIG. 13(B), vibration is applied to the micropipette 63 in its longitudinal direction. After that, as shown in FIG. 13(C), when the tip of the micropipette is inserted into the fertilized egg 71 to a distance b or more (that is, when the cell membrane is about to be pierced after the zona pellucida is pierced, and when the nuclear membrane is about to be pierced after the cell membrane is pierced), the vibration pattern of the micropipette 63 is changed. When the micropipette 63 is being pulled back, the reverse process can be performed.

Next, the control of the vibration direction of the vibrator is explained below.

In the real situation where the microinjection is performed, the tip of the micropipette is usually bent so as to easily introduce the micropipette into a fertilized egg contained in a container. (See the Patent Document 5 described above.) In such case where the tip of the micropipette is bent, if the control method of the vibrator described above is applied, the tip of the micropipette can be vibrated obliquely, thereby possibly resulting in undesirable vibration.

Therefore, in order to perform the microinjection optimally, it is preferable that the vibration direction at the tip of the micropipette is controlled intentionally.

Figure 14:
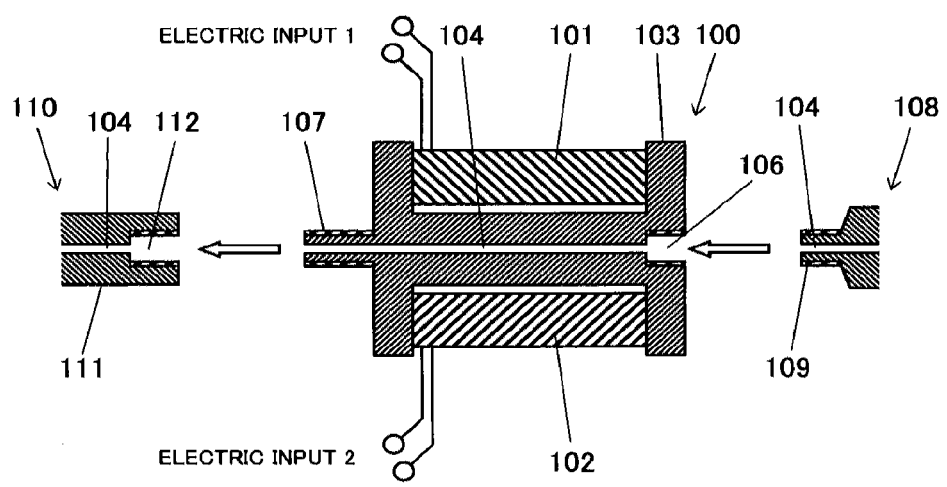
FIG. 14 is a schematic diagram showing a structure of a vibrator of a vibration type microinjection device according to a second embodiment of the present invention.
Figure 15:
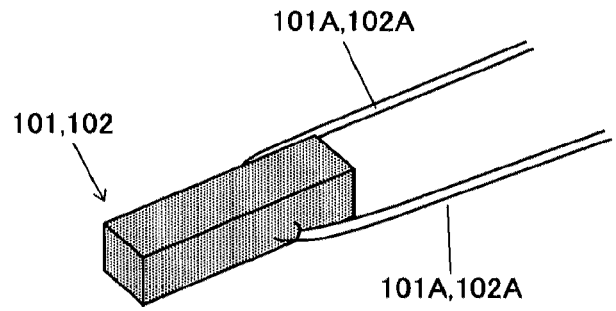
FIG. 15 is a perspective view of a rectangular pillar shape piezoelectric actuator body of a vibrator of a vibration type microinjection device according to the second embodiment of the present invention.
Figure 16:
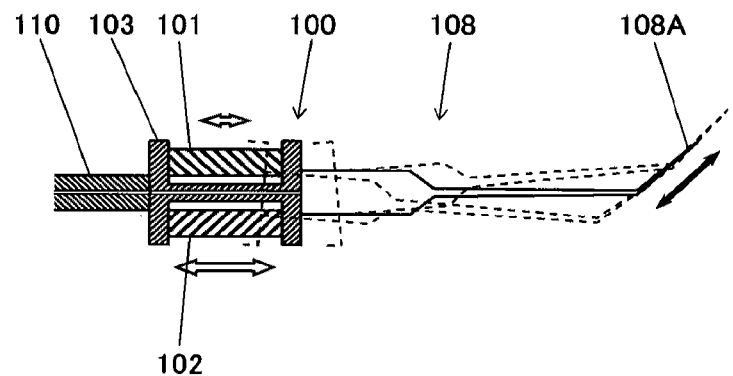
FIG. 16 shows an image of the vibration control when a tip of a micropipette is bent in the vibration type microinjection device according to the second embodiment of the present invention.

FIG. 14 is a schematic diagram illustrating a structure of a vibrator of a vibration type microinjection device according to a second embodiment of the present invention. FIG. 15 is a perspective view of a rectangular pillar shape piezoelectric actuator body of the vibrator of the vibration type microinjection device. FIG. 16 shows an image of the vibration control when the tip of the micropipette is bent in the vibration type microinjection device.

In these figures, a vibrator 100 comprises at least a plurality of rectangular pillar shape piezoelectric actuators 101, 102, as shown in FIG. 15, arranged in parallel, and a housing 103 in which these piezoelectric actuators 101, 102 are installed. At the center of the housing 103, a narrow path 104 is formed. On one end of the housing 103, a fitting concave 106 is formed to be fitted with the base part of the micropipette 108, and on the other end of the housing 103, a fitting convex 107 is formed to fit an injection controller part 110. Furthermore, on the base part of the micropipette 108, a fitting convex 109 to fit the fitting concave 106 described above and a path 104 are formed. At an end portion 111 of the injection controller part 110, a fitting concave 112 to be fitted with the fitting convex 107 described above and a path 104 are formed. When the injection controller part 110, the vibrator 100 and the micropipette 108 are all connected, the path 104 is brought into line on their center axis. Four rectangular pillar shape piezoelectric actuators are used here as two sets of piezoelectric actuators. That is to say, each one of the sets is comprised of two rectangular pillar shape piezoelectric actuators. The two rectangular pillar shape piezoelectric actuators in each one of the sets are connected electrically in parallel or in series with each other. FIG. 15 shows said one set of piezoelectric actuators 101 or 102 in FIG. 14. Moreover, the shape of the piezoelectric actuator is not limited to a rectangular pillar shape, but it may be a circular pillar shape or an elliptical pillar shape. That is to say, any pillar shapes are acceptable.

Thus, although the basic structure of this embodiment is the same as the first embodiment described above, at least four piezoelectric actuators are used and they vibrate individually by applying their respective electric signals in this embodiment. 101A, 102A are lead wires of respective sets of piezoelectric actuators 101, 102.

Furthermore, in order to apply longitudinal vibration to the tip 108A of the micropipette in its longitudinal direction in the case where the tip 108A of the micropipette 108 is bent, the two sets of piezoelectric actuators 101, 102 are provided with different vibrations having the same frequency but having different amplitudes, phases and offset values, which all are adjusted mutually, and thereby, vibration approximately in the longitudinal direction of the bent tip 108A of the micropipette can be strengthened as shown in FIG. 16.

Similarly, vibration perpendicular to the longitudinal direction of the bent tip 108A of the micropipette can be also strengthened. In particular, by adjusting the phase difference at around 90°, circular or elliptical motion can be also given to the bent tip 108A of the micropipette.

Figure 17:
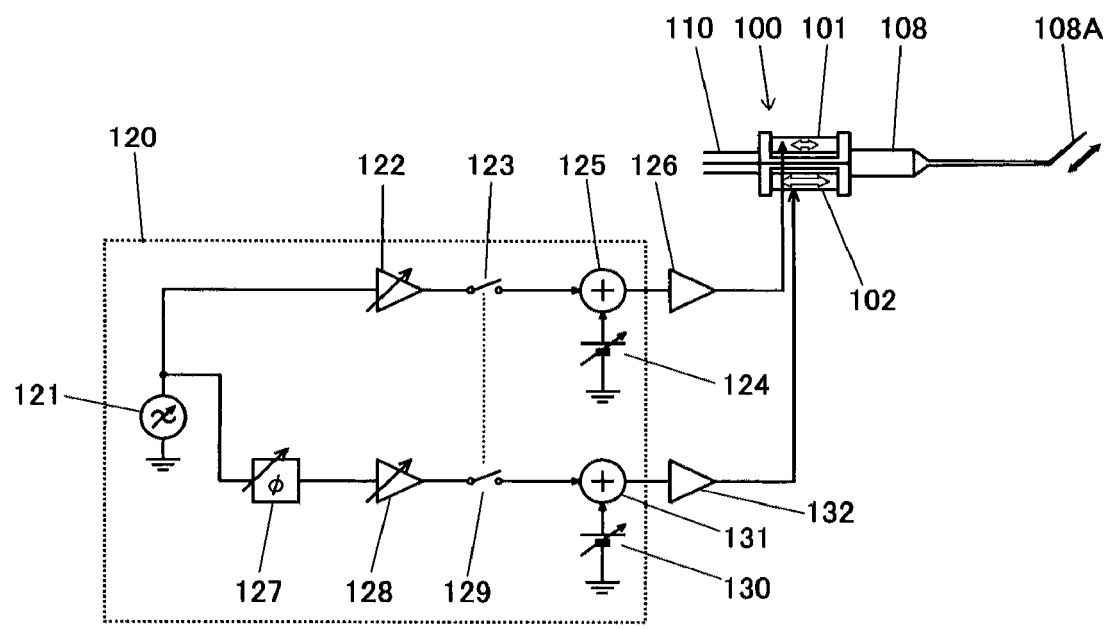
FIG. 17 is a configuration diagram of a driving device for controlling vibration direction of a vibrator according to the second embodiment of the present invention.

FIG. 17 is a configuration diagram of the driving device for the purpose of control for vibration direction of the vibrator according to the second embodiment of the present invention.

In this figure, a structure of the vibrator 100 is the same as that shown in FIG. 14 and FIG. 16.

A signal control device 120 for supplying signal to the vibrator 100 is composed of a variable frequency oscillator 121, a first amplifier for amplitude adjustment 122 connected to the variable frequency oscillator 121, a first foot switch 123 connected to the first amplifier for amplitude adjustment 122, a first DC source for offset adjustment 124, a first adder 125 to which a signal from the first foot switch 123 and an output from the first DC source for offset adjustment 124 are inputted. This first adder 125 is connected to a first DC-coupling power amplifier 126, and an output signal from the first power amplifier 126 is applied to a first set of piezoelectric actuators 101. On the other hand, the signal control device 120 for supplying signal to the vibrator 100 is further composed of a variable phase shifter (0°-360°) 127 on a separated branch from the variable frequency oscillator 121, a second amplifier for amplitude adjustment 128 connected to the variable phase shifter 127, a second foot switch 129 which is connected to the second amplifier for amplitude adjustment 128 and which is operated simultaneously with the first foot switch 123, a second DC source for offset adjustment 130, and a second adder 131 to which a signal from the foot switch 129 and an output from the second DC source for offset adjustment 130 are inputted. The second adder 131 is connected to a second DC-coupling power amplifier 132, and an output signal from the second power amplifier 132 is applied to a second set of piezoelectric actuators 102.

Thus, signals from the common variable frequency oscillator 121 are sent directly and through the 0~360° variable phase shifter 127 to the amplifiers for amplitude adjustment 122 and 128, respectively, and after that, outputs from the respective DC sources for offset adjustments 124 and 130 are added to the respective signals in order to drive the two sets of actuators 101, 102 independently. Thereby, vibration of the tip 108A of the micropipette in its longitudinal direction is realized.

Figure 18:
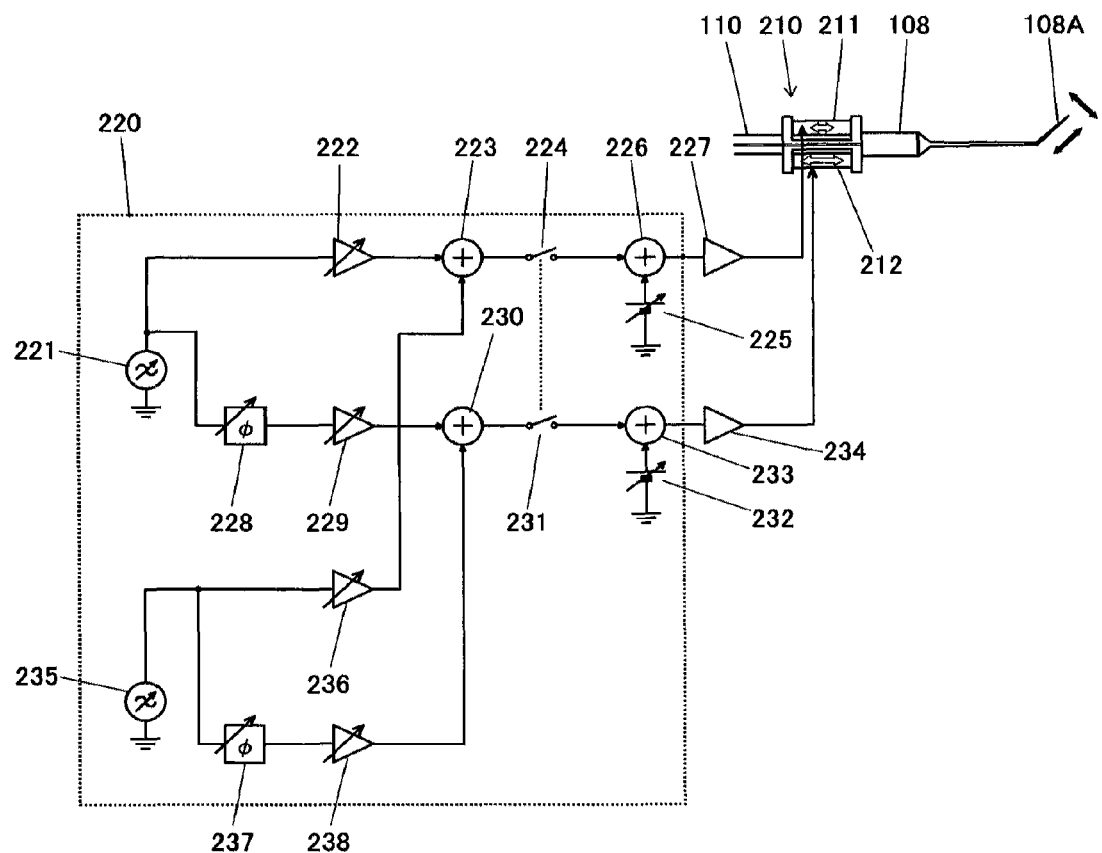
FIG. 18 is a configuration diagram of a driving device for controlling the vibrator so as to simultaneously vibrate the tip of a micropipette in two directions according to a third embodiment of the present invention.

FIG. 18 is a configuration diagram of a driving device for controlling the vibrator so as to simultaneously vibrate the tip of a micropipette in two directions according to a third embodiment of the present invention.

In this figure, a structure of a vibrator 210 is the same as that shown in FIG. 14 and FIG. 16.

A signal control device 220 to supply signals to the vibrator 210 comprises a first variable frequency oscillator 221, a first amplifier for amplitude adjustment 222 connected to the first variable frequency oscillator 221, and a first adder 223 connected to the first amplifier for amplitude adjustment 222. In addition, an output signal from a second variable frequency oscillator 235 and a second amplifier for amplitude adjustment 236 connected to the second variable frequency oscillator 235 is applied to the first adder 223. The signal control device 220 further comprises a first foot switch 224 connected to the first adder 223, a first DC source for offset adjustment 225, and a second adder 226 to which a signal from the first foot switch 224 and an output from the first DC source for offset adjustment 225 are inputted. The adder 226 is connected to a first DC-coupling power amplifier 227, and an output signal from the power amplifier 227 is applied to a first set of piezoelectric actuators 211. Further on the other hand, an output from a first variable phase shifter (0°-360°) 228 on a separated branch from the first variable frequency oscillator 221 is applied to a third adder 230 through a third amplifier for amplitude adjustment 229. Also to the third adder 230, an output signal from a second variable phase shifter (0°-360°) 237 which is on a separated branch from the second variable frequency oscillator 235 and a fourth amplifier for amplitude adjustment 238 connected to the second variable phase shifter 237 is applied. The third adder 230 is connected to a second foot switch 231 which operates simultaneously with the first foot switch 224. Moreover, a fourth adder 233 to which a signal from the foot switch 231 and an output from a second DC source for offset adjustment 232 are inputted is provided. The adder 233 is connected to a second DC-coupling power amplifier 234, and an output from the second power amplifier 234 is applied to a second set of piezoelectric actuators 212.

By providing two signal control circuits for controlling the vibrations in this way, vibrations parallel and perpendicular to the longitudinal direction of the tip 108A of the micropipette can be strengthened at different frequencies and amplitudes.

In this case, one of the vibration frequencies may be in the ultrasonic range. Furthermore, the methods of changeover and/or multiplication of frequencies as shown in FIG. 9 and FIG. 10 can also be utilized. A personal computer and two DA converters as shown in FIG. 11 can also be used as a signal generation part.

When the tip of the micropipette is bent, the bending is performed on site in each case. Therefore, the bending position, angle and the like vary from one pipette to another. In order to apply optimal vibration according to the conditions of the micropipette, frequency, phase difference, amplitude, and offset voltage and so on must be adjusted individually. Therefore, the configuration as explained below is adopted.

Figure 19:
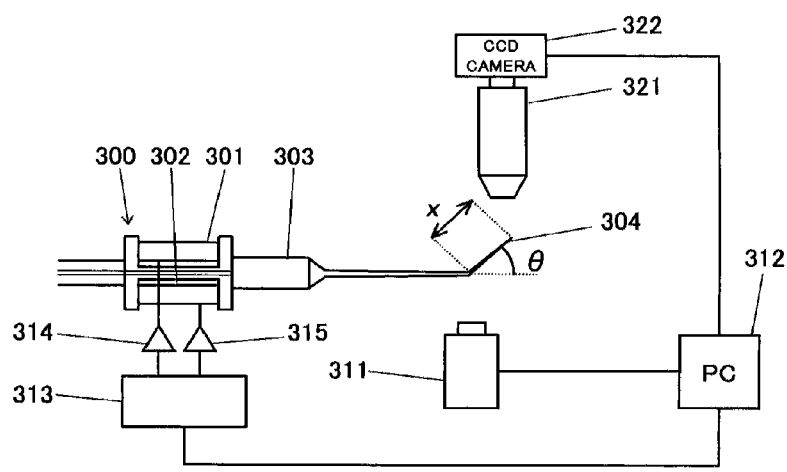
FIG. 19 is a schematic diagram of a control system of vibration to control the vibrations differently depending on a shape of a bent tip of a micropipette by detecting the shape of the tip of the micropipette according to a fourth embodiment of the present invention.

FIG. 19 is a schematic diagram showing a system for detecting the shape of the bent tip of the micropipette to apply optimal vibration according to the shape of the tip of the micropipette according to a fourth embodiment of the present invention.

In this figure, 300 is a vibrator having a plurality of piezoelectric actuators 301, 302, and 303 is a micropipette connected to the vibrator 300, 304 is a bent tip of the micropipette 303, θ is a bending angle of the bent tip 304, 311 is a first CCD camera to take an image of the bent tip 304 of the micropipette 303, 322 is a second CCD camera to detect images obtained when the tip 304 of the micropipette is inserted into a fertilized egg. Image information from these CCD cameras 311, 322 is taken into a personal computer 312, and information on the bending condition of the bent tip 304 of the micropipette 303 and the insertion state of the micropipette 303 into the fertilized egg is detected. Based on the detected information on the bending state and the insertion state into the fertilized egg of the micropipette, a signal control device 313 is adjusted, and the adjusted output signals are applied to each of the plurality of piezoelectric actuators 301, 302 through respective power amplifiers 314, 315, thereby enabling precise control of vibrations of the bent to the bent tip 304 of the micropipette 303. In addition, the second CCD camera 322 for detecting the insertion state of the micropipette into the fertilized egg must be provided with a microscope 321. On the other hand, a microscope is not provided to the first CCD camera 311 for detecting the bending state of the micropipette 303. In order to detect the bending state of the micropipette 303 accurately, images must be taken from the side.

As shown in FIG. 19, an image of the bent tip 304 of the micropipette 303 is taken from the lateral direction with the CCD camera 311, the image data are transferred to the personal computer 312, and the position (x) and the angle (θ) are determined by image analysis using a personal computer. By comparing these values with the reference data, which have been obtained in advance experimentally and been registered in the database of the personal computer, and by executing processing such as interpolation, the signals from the signal control device 313 are determined.

The present invention is not limited to the embodiments described above. Various modifications are possible based on the spirit of the present invention. These modifications are not excluded from the scope of the present invention.

The present invention has advantages as described below.

(1) By using a single or plural piezoelectric actuators (multilayer type piezoelectric actuators), vibration with an amplitude ranging from submicron to micrometer and a frequency ranging from audible to ultrasonic range can be applied.

(2) By setting the direction of vibration to the longitudinal direction of a micropipette and by adjusting conditions of the vibration, the micropipette penetrates the processing object smoothly.

(3) Especially in the case where the tip of the micropipette is bent, the use of a plurality of piezoelectric actuators achieves a vibration approximately parallel or perpendicular to the longitudinal direction of the bent tip portion of the micropipette and furthermore a circular or elliptical vibration (movement) of the bent tip.

(4) When the processing object is a fertilized egg, different types of membranes, i.e. a zona pellucida, a cell membrane and a nuclear membrane, can be pierced optimally by instantaneous changeover of frequency, amplitude, phase and others of vibration applied to the tip of the micropipette according to which membrane is about to be pierced.

(5) By applying vibrations of plurality of frequencies simultaneously or differently according to the direction, precision and efficiency of injection can be improved.

(6) When the tip of the micropipette is bent, the bending is performed on site in each case. Therefore, the bending position, angle and the like vary from one pipette to another. In order to apply vibrations to the micropipette in the optimal direction, the image of the micropipette is processed with a personal computer to determine the position and the angle of the bending of the micropipette, and by comparing the result with the reference data already registered, it can be possible to determine the optimal amplitudes, frequencies and so on.

(7) When the processing object is a fertilized egg, vibration of the pipette is necessary only when a zona pellucida, a cell membrane, and a nuclear membrane are pierced. To achieve this aim, a foot switch can be used, thus applying vibration efficiently. Also, by using a foot switch of two-stage changeover type or a foot pedal of potentiometer type, changeover of frequency and amplitude becomes possible. Furthermore, an image under a microscope is processed with a personal computer to determine the relative positions between the fertilized egg and the tip of the micropipette after their contours are extracted. By automatically controlling the state of vibration based on the calculated results, efficiency in microinjection can be further improved.

Industrial Applicability

Vibration type microinjection device according to the present invention can be utilized as a microinjection tool for genetic recombination and the like.

The invention claimed is:

1. A vibration type microinjection device comprising:
a vibrator which is connected in series between a micropipette and an injection controller part, the vibrator comprising: a housing having an open path extending longitudinally through the center of the housing, the housing being made of elastically deformable material; and a cylindrical piezoelectric actuator installed in the housing around the open path to apply vibration to the housing;
a signal control device for controlling an electric signal applied to the piezoelectric actuator,
wherein vibration is applied in the longitudinal direction of the micropipette via the vibrator by inputting an electric signal to the piezoelectric actuator, and
wherein the signal control device comprises a variable frequency oscillator, an amplifier for amplitude adjustment connected to the variable frequency oscillator, a switch connected to the amplifier for amplitude adjustment, an adder to which the switch and a variable DC source for offset adjustment are connected, and a power amplifier which is connected to the adder and which supplies an electric signal to the piezoelectric actuator.

2. The vibration type microinjection device according to claim 1, wherein:
the variable frequency oscillator is a plurality of variable frequency oscillators; and
the switch is a switch of a change-over type, whereby changeover to any one of the plurality of the variable frequency oscillators is carried out by switching the switch.

3. The vibration type microinjection device according to claim 1, wherein:
the variable frequency oscillator is a plurality of variable frequency oscillators;
the amplifier for amplitude adjustment is a plurality of amplifiers connected to the plurality of variable frequency oscillators; and
the adder comprises;
a first adder to which output signals from the plurality of amplifiers for amplitude adjustment are inputted simultaneously with the switch connected to the first adder; and
a second adder connected to the switch with the power amplifier connected to the second adder to supply an electric signal to the piezoelectric actuator, thereby simultaneously supplying vibration with a plurality of frequencies.

4. The vibration type microinjection device according to claim 1, wherein the vibration has an amplitude on order of sub-micron to micron and a frequency within the range from audible to ultrasonic range.

5. The vibration type microinjection device according to claim 1 further comprising:
a tube extending longitudinally through the housing and having an interior defining the open path, the tube being arranged within the housing radially spaced from and concentric with the cylindrical piezoelectric actuator.

6. The vibration type microinjection device according to claim 5, wherein:
the tube is open at opposing longitudinal ends of the housing;
the micropipette has a lumen in communication with the open path and is connected with the tube at one of the opposing longitudinal ends of the housing; and
the injection controller part has a central passageway in communication with the open path and is connected with the tube at the other of the opposing longitudinal ends of the housing.

7. A vibration type microinjection device comprising:
a vibrator which is connected in series between a micropipette and an injection controller part, the vibrator comprising: a housing having an open path extending longitudinally through the center of the housing, the housing being made of elastically deformable material; and a cylindrical piezoelectric actuator installed in the housing around the open path to apply vibration to the housing;
a signal control device for controlling an electric signal applied to the piezoelectric actuator,
wherein vibration is applied in the longitudinal direction of the micropipette via the vibrator by inputting an electric signal to the piezoelectric actuator, and wherein the signal control device comprises:
a multiple change-over type switch;
a circuit for applying bias voltage connected to the switch;
a computer connected to the circuit for applying bias voltage;
a DA converter connected to the computer; and
a power amplifier which is connected to the DA converter and which supplies an electric signal to the piezoelectric actuator.

8. A vibration type microinjection device comprising:
a vibrator which is connected in series between a micropipette and an injection controller part, the vibrator comprising: a housing having an open path extending longitudinally through the center of the housing, the housing being made of elastically deformable material; and a cylindrical piezoelectric actuator installed in the housing around the open path to apply vibration to the housing;
a signal control device for controlling an electric signal applied to the piezoelectric actuator in the longitudinal direction of the micropipette via the vibrator;
a microscope with an imaging device to take an image of the tip of the micropipette;
an image input interface to input the image from the imaging device;
wherein the signal control device comprises:
a computer to input a digital output signal from the image input interface;
a DA converter connected to the computer; and
a power amplifier which is connected to the DA converter and which supplies the electric signal to the piezoelectric actuator, wherein the electric signal from the power amplifier is controlled according to the position of a tip part of the micropipette.

9. A vibration type microinjection device comprising:
a vibrator which is connected in series between a micropipette with a bent tip and an injection controller part, the vibrator comprising: a housing having an open path extending through the center of the housing, the housing being made of elastically deformable material; and a plurality of pillar-shaped piezoelectric actuators mounted in the housing around the open path;
a signal control device for controlling electric signals applied to the piezoelectric actuators,
wherein vibration is applied at least in the longitudinal direction of the bent tip of the micropipette via the vibrator by inputting electric signals to the piezoelectric actuators, and
wherein the signal control device comprises a variable frequency oscillator, a first amplifier for amplitude adjustment connected to the variable frequency oscillator, a first switch connected to the first amplifier for amplitude adjustment, a first adder connected to the first switch and a first variable DC source for offset adjustment, a variable phase shifter connected to the variable frequency oscillator, a second amplifier for amplitude adjustment connected to the variable phase shifter, a second switch which is connected to the second amplifier for amplitude adjustment and which operates simultaneously with the first switch, a second adder connected to the second switch and a second variable DC source for offset adjustment, a first power amplifier connected to the first adder and a first piezoelectric actuator, and a second power amplifier connected to the second adder and a second piezoelectric actuator.

10. The vibration type microinjection device according to claim 9 wherein:
the pillar shaped piezoelectric actuators are mounted in parallel within the housing and are coextensive with the longitudinal dimension of the interior of the housing.

11. The vibration type microinjection device according to claim 9 further comprising:

a tube extending longitudinally through the housing and having an interior defining the open path, the tube being arranged within the housing radially spaced from the plural piezoelectric actuators.

12. The vibration type microinjection device according to claim 11, wherein:

the tube is open at opposing longitudinal ends of the housing;

the micropipette has a lumen in communication with the open path and is connected with the tube at one of the opposing longitudinal ends of the housing; and the injection controller part has a central passageway in communication with the open path and is connected with the tube at the other of the opposing longitudinal ends of the housing.

13. A vibration type microinjection device comprising:

a vibrator which is connected in series between a micropipette with a bent tip and an injection controller part, the vibrator comprising: a housing having an open path extending through the center of the housing, the housing being made of elastically deformable material; and a plurality of pillar-shaped piezoelectric actuators mounted in the housing around the open path;

a signal control device for controlling electric signals applied to the piezoelectric actuators, wherein vibration is applied at least in the longitudinal direction of the bent tip of the micropipette and in the direction perpendicular to the longitudinal direction of the bent tip of the micropipette via the vibrator by inputting electric signals to the piezoelectric actuators, and wherein the signal control device comprises:

a first variable frequency oscillator;

a first amplifier for amplitude adjustment connected to the first variable frequency oscillator;

a first adder which is connected to the first amplifier for amplitude adjustment and to which an output signal from a second amplifier for amplitude adjustment connected to a second variable frequency oscillator is applied;

a first switch connected to the first adder; and a second adder connected to the first switch and a first variable DC source for offset adjustment;

a first variable phase shifter connected to the first variable frequency oscillator;

a third amplifier for amplitude adjustment connected to the first variable phase shifter;

a third adder which is connected to the third amplifier for amplitude adjustment and to which an output signal from a second variable phase shifter to which the second variable frequency oscillator is connected and a fourth amplifier for amplitude adjustment connected to the second variable phase shifter is applied;

a second switch which is connected to the third adder and which operates simultaneously with the first switch;

a fourth adder connected to the second switch and a second variable DC source for offset adjustment;

a first power amplifier which is connected to the second adder and which supplies an output signal to a first piezoelectric actuator; and a second power amplifier which is connected to the fourth adder and which supplies an output signal to a second piezoelectric actuator.

\* \* \* \* \*